United States Patent
Chang et al.

(10) Patent No.: US 11,529,258 B2
(45) Date of Patent: Dec. 20, 2022

(54) ADJUSTABLE FLOW GLAUCOMA SHUNTS AND ASSOCIATED SYSTEMS AND METHODS

(71) Applicant: Shifamed Holdings, LLC, Campbell, CA (US)

(72) Inventors: Robert Chang, Belmont, CA (US); Katherine Sapozhnikov, Campbell, CA (US); Claudio Argento, Felton, CA (US); Tom Saul, Moss Beach, CA (US); Richard Lilly, San Jose, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/606,661

(22) PCT Filed: Jan. 22, 2021

(86) PCT No.: PCT/US2021/014774
§ 371 (c)(1),
(2) Date: Oct. 26, 2021

(87) PCT Pub. No.: WO2021/151007
PCT Pub. Date: Jul. 29, 2021

(65) Prior Publication Data
US 2022/0142818 A1 May 12, 2022

Related U.S. Application Data

(60) Provisional application No. 62/965,117, filed on Jan. 23, 2020.

(51) Int. Cl.
*A61F 9/007* (2006.01)

(52) U.S. Cl.
CPC .. *A61F 9/00781* (2013.01); *A61F 2250/0004* (2013.01)

(58) Field of Classification Search
CPC ............... A61F 9/00781; A61F 9/0017; A61F 2210/0014; A61F 2009/00981; A61M 27/002; A61M 2210/0612
See application file for complete search history.

(56) References Cited

U.S. PATENT DOCUMENTS

| 4,401,107 A | 8/1983 | Harber et al. |
| 4,595,390 A | 6/1986 | Hakim et al. |

(Continued)

FOREIGN PATENT DOCUMENTS

| AU | 2014201621 B2 | 3/2016 |
| AU | 2016201445 B2 | 3/2016 |

(Continued)

OTHER PUBLICATIONS

International Search Report and Written Opinion received for International PCT Application No. PCT/US2021/014774, filed on Jan. 22, 2021; Applicant: Shifamed Holdings, LLC; dated May 12, 2021, 10 pages.

(Continued)

*Primary Examiner* — Leslie R Deak
(74) *Attorney, Agent, or Firm* — Perkins Coie LLP

(57) ABSTRACT

The present technology is directed to adjustable shunts for treating glaucoma. In particular, some embodiments provide shunts having a plurality of individually actuatable flow control elements that can control the flow of fluid through associated ports and/or flow lumens. For example, each individually actuatable flow control element can be actuated to block and/or unblock a corresponding port and/or flow lumen. Accordingly, the shunts described herein can be manipulated into a variety of configurations that provide (Continued)

different drainage rates based on whether the ports and/or flow lumens are blocked or unblocked, therefore providing a titratable glaucoma therapy for draining aqueous from the anterior chamber of the eye.

44 Claims, 6 Drawing Sheets

(56) References Cited

U.S. PATENT DOCUMENTS

| | | |
|---|---|---|
| 5,070,697 A | 12/1991 | Van Zeggeren |
| 5,123,906 A | 6/1992 | Kelman |
| 5,300,020 A | 4/1994 | L'Esperance, Jr. |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,364,564 B2 | 4/2008 | Sniegowski et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,440 B2 | 6/2012 | Guarnieri |
| 8,298,240 B2 | 10/2012 | Giger et al. |
| 8,308,701 B2 | 11/2012 | Horvath et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Romoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,516 B2 | 11/2015 | Horvath et al. |
| 9,226,851 B2 | 1/2016 | Gunn |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Rangel-Friedman et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,335,030 B2 * | 7/2019 | Alhourani ............... A61B 3/16 |
| 10,369,048 B2 | 8/2019 | Horvath et al. |
| 10,405,903 B1 | 9/2019 | Biesinger et al. |
| 10,342,703 B2 | 11/2019 | Siewert et al. |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,959 B2 | 1/2020 | Horvath |
| 10,524,958 B2 | 3/2020 | Camras et al. |
| 10,596,035 B2 | 4/2020 | Stergiopulos et al. |
| 10,758,412 B2 | 4/2020 | Velasquez |
| 11,122,975 B2 | 1/2021 | Rodger et al. |
| 10,912,675 B2 | 2/2021 | Lubatschowski |
| 11,166,847 B2 | 2/2021 | Badawi et al. |
| 10,952,897 B1 | 3/2021 | Smith |
| 10,960,074 B2 | 3/2021 | Berdahl |
| 11,039,954 B2 | 6/2021 | Cohen et al. |
| 11,058,581 B2 | 7/2021 | Mixter et al. |
| 11,065,154 B1 | 7/2021 | Sponsel et al. |
| 11,083,624 B2 | 8/2021 | Stein et al. |
| 11,166,848 B2 | 11/2021 | Mixter et al. |
| 11,166,849 B2 | 11/2021 | Mixter et al. |
| 11,291,585 B2 | 4/2022 | Schultz et al. |
| 2001/0011585 A1 | 8/2001 | Cassidy et al. |
| 2002/0177891 A1 | 11/2002 | Miles et al. |
| 2002/0193725 A1 | 12/2002 | Odrich |
| 2003/0127090 A1 | 7/2003 | Gifford et al. |
| 2003/0163079 A1 | 8/2003 | Burnett |
| 2004/0010219 A1 | 1/2004 | McCusker et al. |
| 2004/0254520 A1 | 12/2004 | Porteous et al. |
| 2005/0049578 A1 | 3/2005 | Tu et al. |
| 2006/0155300 A1 | 7/2006 | Stamper et al. |
| 2007/0010837 A1 | 1/2007 | Tanaka |
| 2007/0078371 A1 | 4/2007 | Brown et al. |
| 2007/0088432 A1 | 4/2007 | Solovay et al. |
| 2008/0077071 A1 | 3/2008 | Yaron et al. |
| 2008/0119891 A1 | 5/2008 | Miles et al. |
| 2008/0125691 A1 * | 5/2008 | Yaron ............... A61F 9/00781 604/9 |
| 2008/0228127 A1 | 9/2008 | Burns et al. |
| 2009/0036818 A1 | 2/2009 | Grahn et al. |
| 2009/0243956 A1 | 10/2009 | Keilman et al. |
| 2009/0326517 A1 | 12/2009 | Bork et al. |
| 2010/0234791 A1 | 9/2010 | Lynch et al. |
| 2010/0241077 A1 | 9/2010 | Geipel et al. |
| 2011/0105986 A1 | 5/2011 | Bronstein et al. |
| 2012/0065570 A1 | 3/2012 | Yeung et al. |
| 2012/0089073 A1 | 4/2012 | Cunningham, Jr. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |

(56) References Cited

U.S. PATENT DOCUMENTS

| | | |
|---|---|---|
| 2014/0046439 A1 | 2/2014 | Dos Santos et al. |
| 2014/0081195 A1* | 3/2014 | Clauson ............. A61F 9/00781 604/8 |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0313603 A1 | 11/2015 | Bodewadt et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0092775 A1 | 4/2018 | de Juan, Jr. et al. |
| 2018/0147089 A1 | 5/2018 | Horvath et al. |
| 2018/0206878 A1 | 7/2018 | Uspenski et al. |
| 2018/0250166 A1 | 9/2018 | Lubatschowski |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0137736 A1 | 5/2021 | Cavuto et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0160545 A1 | 5/2022 | Mixter et al. |
| 2022/0160546 A1 | 5/2022 | Mixter et al. |
| 2022/0202613 A1 | 6/2022 | Chang et al. |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO9219294 | 11/1992 |
| WO | WO2020231993 | 11/2002 |
| WO | WO2004081613 | 9/2004 |
| WO | WO2007011302 A1 | 1/2007 |
| WO | WO2010111528 | 9/2010 |
| WO | WO2014130574 | 8/2014 |
| WO | WO2016149425 | 9/2016 |

(56) References Cited

FOREIGN PATENT DOCUMENTS

| WO | WO2016196841 A1 | 12/2016 |
|---|---|---|
| WO | WO2018229766 | 12/2018 |
| WO | WO2019018807 | 1/2019 |
| WO | WO2019094004 A1 | 5/2019 |
| WO | WO2019165053 | 8/2019 |
| WO | WO2019172940 | 9/2019 |
| WO | WO2020150663 | 7/2020 |
| WO | WO20200215068 | 10/2020 |
| WO | WO202022391 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO202104312 | 10/2021 |
| WO | WO2021212007 | 10/2021 |
| WO | WO2021230887 | 11/2021 |
| ZA | 201708295 | 5/2020 |

OTHER PUBLICATIONS

International Search Report and Written Opinion received for PCT Application No. PCT/US18/43158, filed on Jul. 20, 2018, Applicant: Shifamed Holdings, LLC, dated Nov. 23, 2018, 12 pages.
International Search Report and Written Opinion received for PCT Application No. PCT/US20/41159, filed on Jul. 8, 2020, Applicant: Shifamed Holdings, LLC, dated Oct. 28, 2020, 13 pages.
International Search Report and Written Opinion received for PCT Application No. PCT/US20/41152, filed on Jul. 8, 2020, Applicant: Shifamed Holdings, LLC, dated Oct. 28, 2020, 13 pages.
International Search Report and Written Opinion received for PCT Application No. PCT/US20/14186, filed on Jan. 17, 2020, Applicant: Shifamed Holdings, LLC, dated Jun. 4, 2020, 13 pages.
International Search Report and Written Opinion received for PCT Application No. PCT/US21/17962, filed on Feb. 12, 2021, Applicant: Shifamed Holdings, LLC, dated Jun. 7, 2021, 12 pages.
International Search Report and Written Opinion received for PCT Application No. PCT/US21/23238, filed on Mar. 19, 2021, Applicant: Shifamed Holdings, LLC, dated Jul. 8, 2021, 10 pages.
International Search Report and Written Opinion received for PCT Application No. PCT/US21/18601, filed on Feb. 18, 2021, Applicant: Shifamed Holdings, LLC, dated Jul. 19, 2021, 12 pages.
International Search Report and Written Opinion received for PCT Application No. PCT/US21/27742, filed on Apr. 16, 2021, Applicant: Shifamed Holdings, LLC, dated Oct. 7, 2021, 13 pages.
International Search Report and Written Opinion received for PCT Application No. PCT/US20/55144, filed on Oct. 9, 2020, Applicant: Shifamed Holdings, LLC, dated Feb. 1, 2021, 16 pages.
International Search Report and Written Opinion received for PCT Application No. PCT/US20/55141, filed on Oct. 9, 2020, Applicant: Shifamed Holdings, LLC, dated Jan. 29, 2021, 11 pages.
International Search Report and Written Opinion received for PCT Application No. PCT/US21/49140, filed on Sep. 3, 2021, Applicant: Shifamed Holdings, LLC, dated Dec. 7, 2021, 22 pages.
International Search Report and Written Opinion received for PCT Application No. PCT/US21/55258, filed on Oct. 15, 2021, Applicant: Shifamed Holdings, LLC, dated Feb. 28, 2022, 18 pages.
International Search Report and Written Opinion received for PCT Application No. PCT/US22/13336, filed on Jan. 21, 2022, Applicant: Shifamed Holdings, LLC, dated Apr. 11, 2022, 9 pages.

* cited by examiner

ADJUSTABLE FLOW GLAUCOMA SHUNTS AND ASSOCIATED SYSTEMS AND METHODS

CROSS-REFERENCE TO RELATED APPLICATIONS

This application is a 35 U.S.C. § 371 U.S. National Phase application of International Patent Application No. PCT/US2021/014774, filed Jan. 22, 2021, which claims priority to U.S. Provisional Patent Application No. 62/965,117, filed Jan. 23, 2020, the disclosures of which are incorporated herein by reference in their entireties.

TECHNICAL FIELD

The present technology generally relates to implantable medical devices and, in particular, to intraocular shunting systems and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye, and may result from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the venous vessels of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
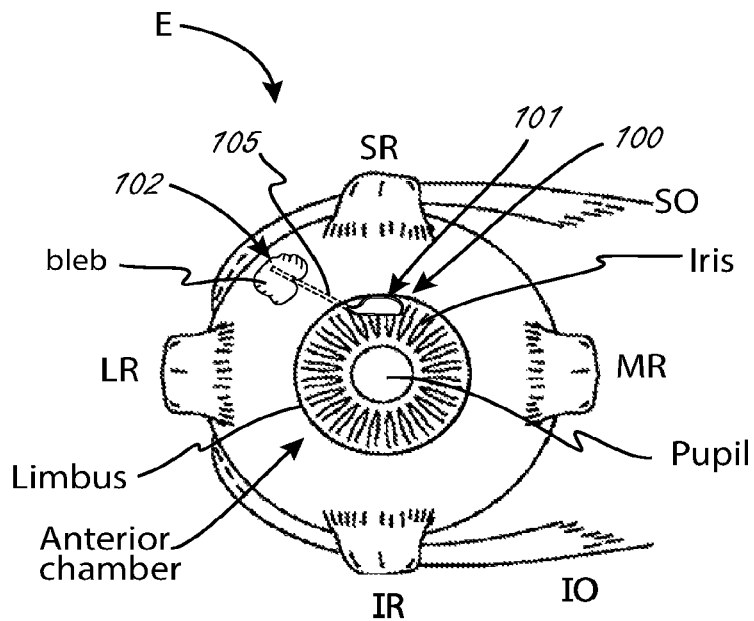
FIG. 1A is a simplified front view of an eye E with an implanted shunt.

The present technology is directed to systems, devices, and methods for treating glaucoma. In particular, some embodiments provide shunts having a plurality of individually actuatable flow control elements that can control the flow of fluid through associated ports and/or channels in the shunt. For example, each individually actuatable flow control element can be actuated to substantially block and/or substantially unblock a corresponding port and/or channel, thereby inhibiting or permitting flow through the port and/or channel. Accordingly, the shunts described herein can be manipulated into a variety of configurations that provide different drainage rates based on whether the ports and/or channels are blocked or unblocked, therefore providing a titratable glaucoma therapy for draining aqueous from the anterior chamber of the eye. In embodiments, the flow control elements can be non-invasively adjusted after the shunt is implanted in the eye to allow for post-implant adjustments.

In many of the embodiments described herein, the shunting systems include ports and/or drainage channels that are configured to provide a different therapy level relative to other ports and/or drainage channels of the system. For example, a first port and/or channel may be associated with a first drainage rate and/or first fluid resistance, a second port and/or channel may be associated with a second drainage rate and/or second fluid resistance, and a third port and/or channel may be associated with a third drainage rate and/or third fluid resistance. As described below, this can be accomplished by having ports and/or drainage channels having different dimensions (e.g., diameters, cross-section areas, lengths, etc.). In some embodiments, the ports and channels are arranged as parallel fluid resistors relative to a primary drainage lumen. In other embodiments, the inflow ports and channels are arranged as serial fluid resistors relative to the primary drainage lumen.

In embodiments in which the inflow ports and channels are arranged as parallel fluid resistors relative to the primary drainage lumen, each individual port may be associated with a discrete and different relative resistance and/or flow. For example, a first port may enable a flow of 1X, a second port may enable a flow of 2X, and a third port may enable a flow of 3X. Moreover, because the ports are arranged as parallel fluid resistors, any combination of ports can be opened (e.g., unblocked) or closed (e.g., blocked, interfered with, etc.) to provide additional discrete relative resistances and/or drainage rates that differ from the discrete relative resistances and flows associated with each individual port. In the foregoing example, both the second and third ports can be opened to provide a flow of 5X. In some embodiments, the relative dimensions of the ports and/or channels can be selected to specifically provide the greatest number of discrete therapy levels. For example, in some embodiments, a ratio between the first drainage rate, second drainage rate, and third drainage rate can be about 1:2:4. Likewise a ratio between the first resistance, the second resistance, and the third resistance can be about 4:2:1. Without being bound theory, this is expected to increase the number of discrete therapy levels the systems can provide, which in turn is expected to enable a healthcare to specifically tailor the therapy level to a particular patient's needs.

In embodiments in which the inflow ports and channels are arranged as serial fluid resistors relative to a main drainage lumen, each individual inflow port may still be associated with a discrete resistance and/or drainage rate. However, unlike embodiments in which the ports are arranged as parallel fluid resistors, the systems cannot be manipulated to achieve a plurality of combined resistances and/or flow rates different than the discrete resistances and/or drainage rates provided by each individual port.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-6.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. Reference throughout this specification to the term "resistance" refers to fluid resistance unless the context clearly dictates otherwise. The terms "drainage rate" and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Intraocular Shunts for Glaucoma Treatment

Glaucoma refers to a group of eye diseases associated with damage to the optic nerve which eventually results in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
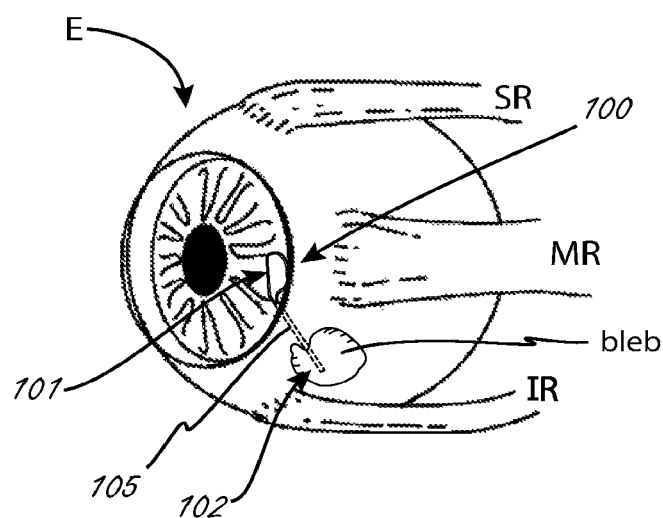
FIG. 1B is an isometric view of the eye capsule of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second, different drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. Details of the implant procedure, the implant devices, and bleb formation are described in greater detail in International Patent Application No. PCT/US20/41152, titled "MINIMALLY INVASIVE BLEB FORMATION DEVICES AND METHODS FOR USING SUCH DEVICES," filed Jul. 8, 2020, the disclosure of which is incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., TOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy from an external energy source (e.g., a laser), such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Adjustable Glaucoma Shunts

Figure 2A:
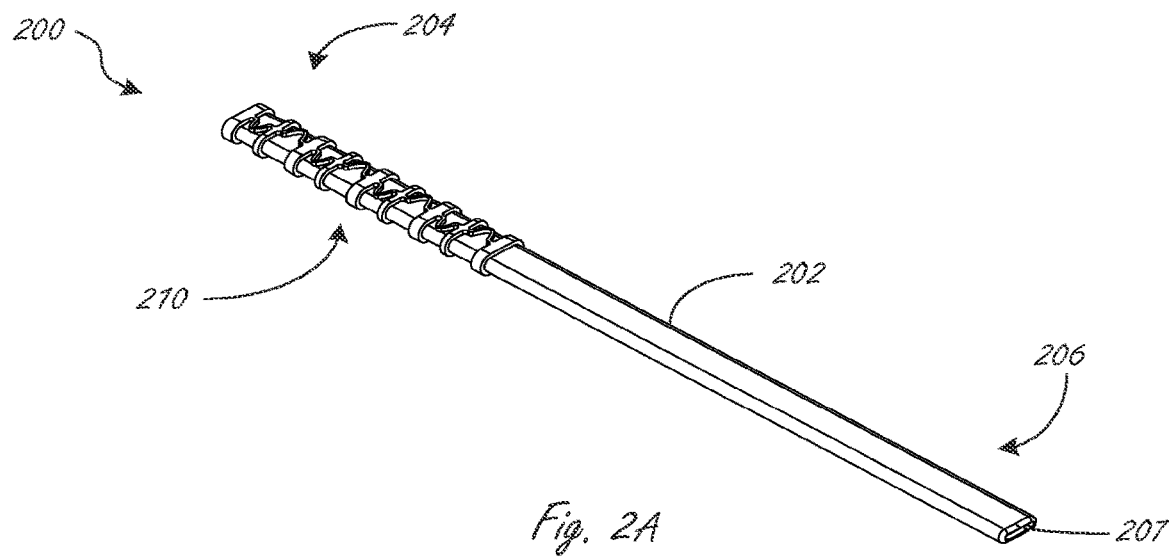
FIGS. 2A-2C illustrate an adjustable shunt configured in accordance with embodiments of the present technology.
Figure 2B:
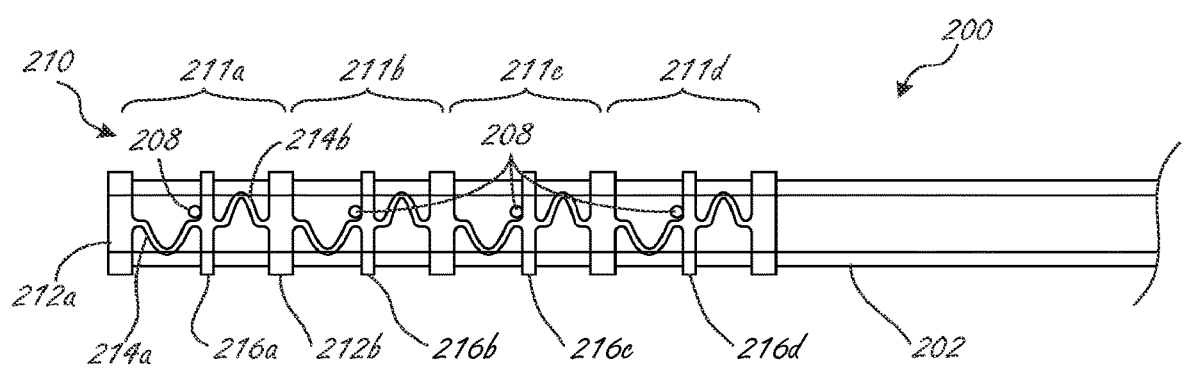
Figure 2C:
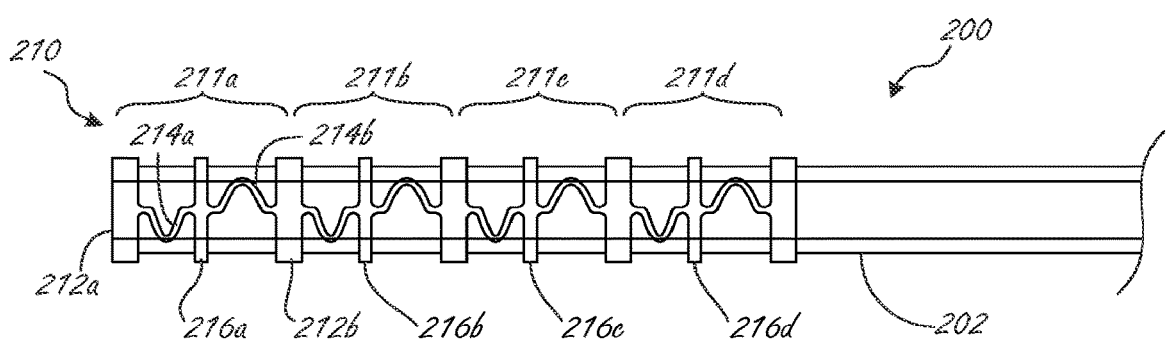

FIGS. 2A-2C illustrate an adjustable shunt 200 ("shunt 200") configured in accordance with embodiments of the present technology. Referring first to FIG. 2A, the shunt 200 includes a drainage element or tube 202 having a first end portion 204 and a second end portion 206 opposite the first end portion 204. The drainage element 202 can have a plurality of inflow ports or apertures (referred to herein as ports 208—shown in FIG. 2B) at or adjacent to the first end portion 204 and an outflow aperture 207 at or adjacent the second end portion 206. The ports 208 can be arranged and/or configured such that they provide the equivalent of a set of parallel fluid resistors accessing a primary lumen of the device. The primary lumen can extend through the drainage element 202 to fluidly connect the plurality of ports 208 and the outflow aperture 207. Accordingly, the shunt 200 can also be referred to as a parallel resistor.

In some embodiments, the drainage element 202 can be relatively flat such that its height is less than its width (e.g., the drainage element 202 has an oval, rectangular, or "D-shaped" cross sectional shape). In such embodiments, the drainage element 202 may have an outer diameter (e.g., height) of about 1000 microns ($\mu m$) or less, about 400 $\mu m$ or less, or about 300 $\mu m$ or less. The drainage element 202 can have an outer diameter value that is between any of the aforementioned values of outer diameter. In some embodiments, the drainage element may have an inner diameter of about 800 $\mu m$ or less, about 300 $\mu m$ or less, or about 200 $\mu m$ or less. The drainage element 202 can have an inner diameter value that is between any of the aforementioned values of inner diameter. In some embodiments, the drainage element 202 can have a length that is about 2 mm, about 2.5 mm, about 5 mm, about 6 mm, about 7 mm, about 8 mm, about 9 mm, about 10 mm, about 15 mm, or about 20 mm. The drainage element 202 can have a length that is between any of the aforementioned values of length. In other embodiments, the drainage element 202 can be substantially cylindrical. Without wishing to be bound by theory, having a relatively flat profile is expected to advantageously reduce interference with native tissue while providing increased stability of the shunt 200.

The shunt 200 can include a flow control mechanism 210 positioned at the first end portion 204 of the drainage element 202. When the shunt 200 is implanted in an eye, the first end portion 204 can reside within an anterior chamber and the second end portion 206 can reside in a desired outflow location (e.g., a bleb space, such as those described in International Patent Application No. PCT/US20/41152, previously incorporated by reference herein). In such embodiments, the flow control mechanism 210 is located within the anterior chamber. In other embodiments, the first end portion 204 can reside within the desired outflow location and the second end portion 206 can reside within the anterior chamber (e.g., fluid would flow from the outflow aperture 207 to the ports 208). In such embodiments, the flow control mechanism 210 is positioned outside of the anterior chamber (e.g., in the bleb space). Regardless of the orientation of the shunt 200, the shunt 200 is configured to drain aqueous from the anterior chamber when the shunt 200 is implanted in the eye. The shunt 200 may optionally have additional features that help secure the shunt 200 in place when implanted in the eye. For example, the shunt 200 can include arms, anchors, plates, or other suitable features (not shown) that can secure the shunt 200 to native tissue. The shunt 200 may also include an outer membrane or cover (e.g., a transparent and/or biocompatible membrane) that encases some or all of the shunt 200.

Referring now to FIGS. 2B and 2C, the flow control mechanism 210 includes a plurality of flow control elements 211a-d arranged along the length of the drainage element 202. Individual flow control elements 211a-d can interface with a corresponding individual port 208, and each flow control element 211a-d can be individually actuatable. Accordingly, as described below, the shunt 200 can be manipulated into any number of configurations with all (FIG. 2C), some, or none (FIG. 2B) of the ports 208 blocked or substantially blocked. The more ports 208 that are unblocked or otherwise accessible, the more fluid is able to drain via the drainage element 202. As described in detail with respect to FIGS. 3A and 3B, the ports 208 can have the same or different dimensions. In some embodiments, the ports 208 are generally regularly spaced apart (e.g., spaced about 1 mm apart). In some embodiments, the ports 208 are spaced to have varied distances between adjacent ports 208. For example, at least two adjacent ports 208 can have a spacing distance that is different than a spacing distance between other ports 208 of the plurality of ports 208.

Each flow control element 211a-d includes a pair of anchors 212 (e.g., the first flow control element 211a includes a first anchor 212a and second anchor 212b) spaced apart along a length of the drainage element 202. In some embodiment, adjacent flow control elements 211a-d may share an anchor. For example, the second anchor 212b anchors both the first flow control element 211a and the second flow control element 211b. The anchors 212 are secured to the drainage element 202 such that at least one of the ports 208 is positioned generally between each pair of anchors. The anchors 212 can be secured to the drainage element 202 or other structure such that they do not move when the flow control elements 211a-d are actuated. For example, the anchors 212 may wrap around a circumference of the drainage element 202 and be secured thereto via a friction fit or other suitable attachment mechanism. In other embodiments, the anchors 212 do not wrap around the full circumference of the drainage element but nevertheless secure the flow control mechanism 210 to the drainage element 202 (e.g., via welding, gluing, or other suitable adhesion techniques).

Each individual flow control element 211a-d further includes a moveable gating element (e.g., flow control element 211a includes a gating element 216a, flow control element 211b includes a gating element 216b, etc., collectively referred to herein as gating element 216), a first actuation element (e.g., flow control element 211a includes a first actuation element 214a) extending between a first anchor (e.g., the first anchor 212a) and the corresponding gating element 216 (e.g., gating element 216a), and a second actuation element (e.g., flow control element 211b includes a second actuation element 214b) extending between a second anchor (e.g., the second anchor 212b) and the corresponding gating element 216. Each gating element 216a-d is configured to interface with (e.g., at least partially block or otherwise form a substantial or full fluid seal with) a corresponding port 208. The actuation elements can be selectively activated to selectively move the corresponding gating element 216 between one or more positions blocking (or partially blocking) the corresponding port 208 and one or more positions unblocking (or at partially unblocking) the corresponding port 208. For example, (a) the gating element 216a of the first flow control element 211a can be moved between a first open position permitting fluid to flow into the drainage element 202 via the corresponding port 208 and a first closed position substantially preventing fluid from flowing into the drainage element 202 via the corresponding port 208, (b) the gating element 216b of the second flow control element 211b can be moved between a second open position permitting fluid to flow into the drainage element 202 via the corresponding port 208, and a second closed position substantially preventing fluid from flowing into the drainage element 202 via the corresponding port 208, (c) the gating element 216c of the third flow control element 211c can be moved between a third open position permitting fluid to flow into the drainage element 202 via the corresponding port 208, and a third closed position substantially preventing fluid from flowing into the drainage element 202 via the corresponding port 208, and (d) the gating element 216d of the fourth flow control element 211d can be moved between a fourth open position permitting fluid to flow into the drainage element 202 via the corresponding port 208, and a fourth closed position substantially preventing fluid from flowing into the drainage element 202 via the corresponding port 208. Although described as "blocking" and "unblocking" the inflow ports when in the closed and open positions, the gating element can also be described as not interfering with and/or imparting a first fluid resistance through the outlet when in the open position and interfering with and/or imparting a second fluid resistance greater than the first fluid resistance when in the closed position.

The gating elements 216 can be moved by actuating the actuation elements 214. For example, actuating the second actuation element 214a can move the gating element 216a in a first direction, and actuating the first actuation element 114b can move the gating element 216a in a second direction generally opposite the first direction. To facilitate the foregoing movement of the gating elements 216, the actuation elements can be composed at least partially of a shape memory material (e.g., a shape memory alloy) or other suitable material that is configured to change shape upon application of energy. For example, in some embodiments the actuation elements are composed of nitinol. In such embodiments, the actuation elements (and/or regions thereof) can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the actuation element or select region thereof may be deformable (e.g., plastic, malleable, compressible, expandable, etc.). In the second material state, the actuation element or select region thereof may have a preference toward a specific preferred geometry (e.g., original geometry, manufactured or fabricated geometry, heat set geometry, etc.). As described below, the actuation elements can be individually and/or selectively transitioned between the first material state and the second material state by applying energy (e.g., heat, light, etc.) to the actuation element to heat the actuation element above a transition temperature (e.g., a phase transition temperature). If the actuation element is deformed relative to its preferred geometry, the transition from the first material state to the second material state can induce a dimensional change in the actuation element. In some embodiments, the dimensional change is an expansion. In some embodiments, the dimensional change is a contraction (e.g., compression). In some embodiments, the energy is applied from an energy source positioned external to the eye (e.g., a laser), which can enable a user to non-invasively adjust the shunt.

The flow control element 211a (e.g., the first actuation element 214a or the second actuation element 214b) can be actuated to move (e.g., translate) the gating element 216a along the axial length of the drainage element 202 between the first anchor 212a and the second anchor 212b. This movement of the gating element 216a can cause it to block (e.g., partially or fully block) and/or unblock (e.g., partially or fully unblock) the associated port 208. For example, in embodiments in which the first actuation element 214a is compressed relative to its preferred geometry, heating the first actuation element 214a above its transition temperature can cause the first actuation element 214a to expand and/or stiffen (thereby expanding in length). Because the first anchor 212a and the second anchor 212b are secured in place (e.g., they do not move relative to the drainage element 202), the first actuation element 214a pushes the gating element 216a away from the first anchor 212a as it expands (and toward the second anchor 212b). As illustrated in FIG. 2B, this can unblock the port 208 that was previously covered by the gating element 216a, thereby permitting flow into (or out of) the port 208. Likewise, heating the second actuation element 214b causes the second actuation element 214b to expand, which pushes the gating element 216a away from the second anchor 212b and back towards the first anchor 212a. As illustrated in FIG. 2C, this can cause the gating element 216a to block the port 208, thereby preventing flow into (or out of) the port 208. Accordingly, the first actuation element 214a and/or the second actuation element 214b can be selectively targeted to block and/or unblock the port 208. In some embodiments, the first actuation element 214a and/or the second actuation element 214b can be actuated to partially block or partially unblock the port 208, rather than completely blocking and/or unblocking the port 208.

In some embodiments, the actuation elements are configured to retain or substantially retain their shape following application of energy. For example, if energy is applied to the first actuation element 214a to transition the first flow control element 211a from the configuration shown in FIG. 2C to the configuration shown in FIG. 2B, the first flow control element 211a can retain the configuration shown in FIG. 2B until further energy is applied to the first flow control element 211a. Accordingly, once the first flow control element 211a is actuated to unblock the corresponding port 208, the corresponding port 208 remains unblocked until further energy is applied to the first flow control element 211a (e.g., by application of energy to the second actuation element 214b). In other embodiments, the actuation elements may exhibit a (e.g., partial) recoil effect, in which the energized actuation element recoils towards an original shape once the application of energy is terminated.

Although the foregoing description is directed to the first flow control element 211a, the components associated with the flow control elements 211b-d can be actuated in a similar manner. Moreover, additional details regarding the operation of shape memory actuators for glaucoma shunts are described in U.S. Patent App. Publication No. 2020/0229982 and International Patent Application Nos. PCT/US20/55144 and PCT/US20/55141, the disclosures of which are incorporated by reference herein in their entireties and for all purposes.

The shunt 200 can be set such that, at body temperature, all, some, or none of the ports 208 are blocked by the corresponding gating elements 216. Accordingly, in some embodiments the shunt 200 can have a base configuration in which all, some, or none of the ports 208 are blocked by the corresponding gating elements 216.

The drainage of aqueous through the shunt 200 can be selectively controlled by selectively blocking and/or unblocking the ports 208 using the flow control elements 211a-d. For example, to provide a first level of therapy having a first drainage rate and a first flow resistance, one of the ports 208 can be accessible/unblocked, while the remaining ports 208 can be inaccessible/blocked. To provide a second level of therapy having a second drainage rate that is greater than the first drainage rate (e.g., a second flow resistance less than the first flow resistance), two of the ports 208 can be accessible/unblocked, while the remaining ports 208 are inaccessible/blocked. As one skilled in the art will appreciate, the flow control elements 211a-d can be actuated such that any combination of ports 208 are blocked or unblocked to provide multiple different therapy levels.

Figure 3A:
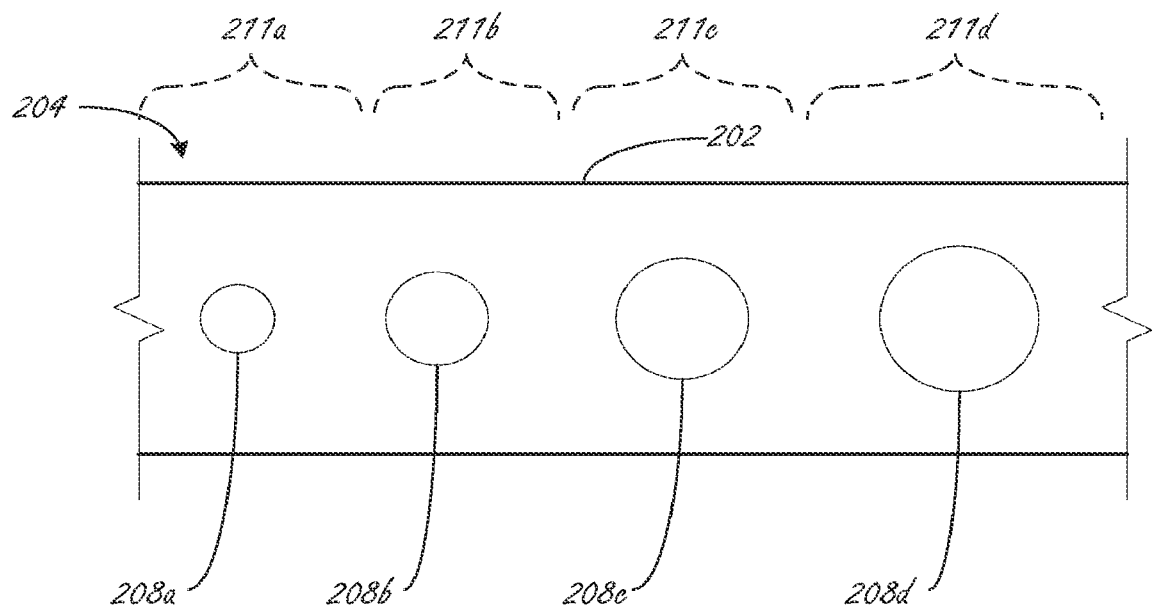
FIG. 3A illustrates select features of the shunt shown in FIGS. 2A-2C configured in accordance with embodiments of the present technology.

To increase the discrete levels of therapy that can be provided by the shunt 200, each port 208 may be configured to provide a different level of therapy (e.g., resistance) relative to each other when the shunt 200 is exposed to a given pressure. FIG. 3A, for example, illustrates an embodiment of the shunt 200 having four ports 208a-d (e.g., apertures), with each port 208a-d having different dimensions. For example, each of the ports 208a-d can have a different diameter that corresponds to a different relative flow rate and/or resistance. In the illustrated embodiment, the port 208a has a first diameter, the port 208b has a second diameter greater than the first diameter, the port 208c has a third diameter greater than the second diameter, and the port 208d has a fourth diameter greater than the third diameter. In some embodiments, the diameter of the ports 208a-d can range between about 4 microns to about 16 microns, from between about 8 microns to about 22 microns, from between about 15 microns to about 60 microns, or from between about 25 microns to about 100 microns, although in other embodiments the diameters of some or all of the ports 208a-d may fall outside the foregoing ranges.

Each of the ports 208a-d can correspond to an individual flow control element 211a-d (omitted in FIG. 3A for clarity). Accordingly, each of the ports 208a-d can be selectively blocked or unblocked by actuating the corresponding flow control element 211a-d, as described above with respect to FIGS. 2A-2C. For example, the flow control elements 211a-d can be actuated such that one or more of the port(s) 208a-d (i) have a first fluid flow cross-section providing a first level of therapy (e.g., when the ports 208a-d are completely open and accessible), or (ii) have a second fluid flow cross-section providing a second level of therapy less than the first level of therapy (e.g., when the port(s) 208a-d are at least partially covered by the corresponding flow control elements 211a-d). Moreover, as provided above, any combination of ports 208a-d can be blocked and any combination of ports 208a-d can be unblocked based on the positioning of the corresponding flow control element 211a-d.

Each of the ports 208a-d can be associated with a desired fluid flow and/or drainage rate relative to other ports 208a-c (e.g., when operating under a given pressure). In some embodiments, the relative drainage rates provided through each individual port 208a-d increases by a common value from the port 208a to the port 208d under a given pressure. For example, the port 208a may be associated with a relative drainage rate of about X, the port 208b may be associated with a relative drainage rate of about 2X, the port 208c may be associated with a relative drainage rate of about 3X, and the port 208d may be associated with a relative drainage rate of about 4X. In such embodiments, the ratio of relative flow rates for the ports 208a-d is 1:2:3:4. In such embodiments, the flow control elements 211a-d can be manipulated to achieve any drainage rate between about X (only the port 208a is unblocked) and about 10X (all of the ports 208a-d are unblocked). In embodiments with only three ports 208a-c, the corresponding flow control elements can be manipulated to achieve any drainage rate between about X (only the port 208a is unblocked) and about 6X (all of the ports 208a-c are unblocked). Table 1 below reflects the relative drainage rate (flow) and associated resistance values for embodiments in which a ratio of the relative flow rates for the ports 208a-d is 1:2:3:4.

TABLE 1

Flow Characteristics for Four Parallel Resistor Ports with Relative Flow Ratio of 1:2:3:4

| Status | Relative Resistance (R) | Relative Flow (Q) |
|---|---|---|
| Open: 208a | 1 | 1 |
| Closed: 208b-d | | |

TABLE 1-continued

Flow Characteristics for Four Parallel Resistor
Ports with Relative Flow Ratio of 1:2:3:4

| Status | Relative Resistance (R) | Relative Flow (Q) |
|---|---|---|
| Open: 208b<br>Closed: 208b, 208c, 208d | 0.5 | 2 |
| Open: 208a, 208b<br>Closed: 208c, 208d | 0.333 | 3 |
| Open: 208c<br>Closed: 208a, 208b, 208d | 0.333 | 3 |
| Open: 208a, 208c,<br>Closed: 208b, 208d | 0.25 | 4 |
| Open: 208d<br>Closed: 208a-c | 0.25 | 4 |
| Open: 208b, 208c<br>Closed: 208a, 208d | 0.2 | 5 |
| Open: 208a, 208d<br>Closed: 208b, 208c | 0.2 | 5 |
| Open: 208a-c<br>Closed: 208d | 0.167 | 6 |
| Open: 208b, 208d<br>Closed: 208a, 208c | 0.167 | 6 |
| Open: 208a, 208b, 208d<br>Closed: 208c | 0.143 | 7 |
| Open: 208c, 208d<br>Closed: 208a, 208b | 0.143 | 7 |
| Open: 208a, 208c, 208d<br>Closed: 208b | 0.125 | 8 |
| Open: 208b-d<br>Closed: 208a | 0.111 | 9 |
| Open: 208a-d<br>Closed: None | 0.1 | 10 |

As reflected in Table 1 above, the same relative flow value (Q) can be attained via different combinations of open and closed ports 208a-d (e.g., flow values of 3, 4, 5, 6, and 7). Therefore, despite having 15 potential combinations of open and closed ports in the illustrated embodiment (16 if all the ports 208a-d are closed), only 10 discrete therapy levels are provided.

In other embodiments, the relative drainage rates through the respective ports 208a-d do not increase by a common value from the port 208a to the port 208d, but rather are selectively sized to achieve a greater number of discrete possible drainage rates (e.g., to avoid overlapping values). For example, in an embodiment having just three ports 208a-c, the port 208a may be associated with a relative drainage rate of about X, the port 208b may be associated with a relative drainage rate of about 2X, and the port 208c may be associated with a relative drainage rate of about 4X. In such embodiments, the ratios of relative flow rates for the ports 208a-c is 1:2:4. The ports 208a-c can be selectively blocked and unblocked by the corresponding flow control elements 311a-c to achieve a variety of desired drainage rates. For example, if only the port 208a is unblocked, the drainage rate is about X, if only the port 208b is unblocked, the drainage rate is about 2X, if both the port 208a and 208b are unblocked, the drainage rate is about 3X, if only the port 208c is unblocked, the drainage rate is about 4X, if the port 208a and 208c are unblocked, the drainage rate is about 5X, if the port 208b and 208c are unblocked, the drainage rate is about 6X, and if ports 208a, 208b, and 208c are all unblocked, the drainage rate is about 7X. Unlike the example provided above, in which a shunt with three ports having a relative drainage ratio of 1:2:3 can provide six discrete potential drainage rates, a shunt with three ports with a relative drainage ratio of 1:2:4 can provide at least seven different potential drainage rates. Accordingly, by varying the dimensions of the ports 208 as described above, a greater number of relative drainage rates can be accomplished with fewer number of ports 208. In embodiments having four ports 208, the port 208d can have a relative drainage rate of about 8X to further increase the number of unique drainage rates possible (e.g., the ratio of relative flow rates for the ports 208a-d is 1:2:4:8). A user can therefore select which ports 208 are blocked and which ports 208 are unblocked to achieve any of the desired drainage rates. Table 2 below reflects the relative drainage rate (flow) and associated resistance values for embodiments in which a ratio of the relative flow rates for the ports 208a-d is 1:2:4:8.

TABLE 2

Flow Characteristics for Four Parallel Resistor
Ports with Relative Flow Ratio of 1:2:4:8

| Status | Relative Resistance (R) | Relative Flow (Q) |
|---|---|---|
| Open: 208a<br>Closed: 208b-d | 1 | 1 |
| Open: 208b<br>Closed: 208b, 208c, 208d | 0.5 | 2 |
| Open: 208a, 208b<br>Closed: 208c, 208d | 0.333 | 3 |
| Open: 208c<br>Closed: 208a, 208b, 208d | 0.25 | 4 |
| Open: 208a, 208c,<br>Closed: 208b, 208d | 0.2 | 5 |
| Open: 208b, 208c<br>Closed: 208a, 208d | 0.167 | 6 |
| Open: 208a-c<br>Closed: 208d | 0.143 | 7 |
| Open: 208d<br>Closed: 208a-c | 0.125 | 8 |
| Open: 208a, 208d<br>Closed: 208b, 208c | 0.111 | 9 |
| Open: 208b, 208d<br>Closed: 208a, 208c | 0.1 | 10 |
| Open: 208a, 208b, 208d<br>Closed: 208c | 0.091 | 11 |
| Open: 208c, 208d<br>Closed: 208a, 208b | 0.083 | 12 |
| Open: 208a, 208c, 208d<br>Closed: 208b | 0.077 | 13 |
| Open: 208b-d<br>Closed: 208a | 0.071 | 14 |
| Open: 208a-d<br>Closed: None | 0.067 | 15 |

Of course, the ratios of relative flow rates for the ports 208a-c can be values other than 1:2:4:8 or 1:2:3:4. In some embodiments, for example, the ratio can be 1:1:1:1, 1:1:2:2, 1:1:1:2, etc. In other embodiments, the ratio may be random (e.g., 1:6:2:3, 4:2:5:1, etc.).

The foregoing flow characteristics can also be described in terms of the resistances provided by each individual port 208a-d. For example, when unblocked or otherwise accessible, the port 208a can have a first resistance, the port 208b can have a second resistance less than the first resistance, the port 208c can have a third resistance less than the second resistance, and the port 208d can have a fourth resistance less than the third resistance. The resistances can have a predetermined ratio. In some embodiments, for example, the ratio of the resistance provided port 208a to the port 208b to the port 208c to the port 208d can be 4:3:2:1, 8:4:2:1, 1:1:1:1, or other ratios. Table 3 below reflects the relative resistance and associated flow for embodiments in which a ratio of the relative resistances for the ports 208a-d is 4:3:2:1. Table 4 below reflects the relative resistance and associated flow for embodiments in which a ratio of the relative resistances for the ports 208a-d is 1:2:4:8.

TABLE 3

Flow Characteristics for Four Parallel Resistor
Ports with Relative Resistance Ratio of 4:3:2:1

| Status | Relative Resistance (R) | Relative Flow (Q) |
| --- | --- | --- |
| Open: 208a<br>Closed: 208b-d | 4 | .25 |
| Open: 208b<br>Closed: 208b, 208c, 208d | 3 | .33 |
| Open: 208a, 208b<br>Closed: 208c, 208d | 1.714 | .583 |
| Open: 208c<br>Closed: 208a, 208b, 208d | 2 | 0.5 |
| Open: 208a, 208c,<br>Closed: 208b, 208d | 1.33 | .75 |
| Open: 208b, 208c<br>Closed: 208a, 208d | 1.2 | .833 |
| Open: 208a-c<br>Closed: 208d | .923 | 1.083 |
| Open: 208d<br>Closed: 208a-c | 1 | 1 |
| Open: 208a, 208d<br>Closed: 208b, 208c | .8 | 1.25 |
| Open: 208b, 208d<br>Closed: 208a, 208c | .75 | 1.333 |
| Open: 208a, 208b, 208d<br>Closed: 208c | .632 | 1.583 |
| Open: 208c, 208d<br>Closed: 208a, 208b | .667 | 1.5 |
| Open: 208a, 208c, 208d<br>Closed: 208b | .571 | 1.75 |
| Open: 208b-d<br>Closed: 208a | .545 | 1.833 |
| Open: 208a-d<br>Closed: None | .48 | 2.083 |

TABLE 4

Flow Characteristics for Four Parallel Resistor
Ports with Relative Resistance Ratio of 8:4:2:1

| Status | Relative Resistance (R) | Relative Flow (Q) |
| --- | --- | --- |
| Open: 208a<br>Closed: 208b-d | 8 | .125 |
| Open: 208b<br>Closed: 208b, 208c, 208d | 4 | .25 |
| Open: 208a, 208b<br>Closed: 208c, 208d | 2.667 | .375 |
| Open: 208c<br>Closed: 208a, 208b, 208d | 2 | 0.5 |
| Open: 208a, 208c,<br>Closed: 208b, 208d | 1.6 | .625 |
| Open: 208b, 208c<br>Closed: 208a, 208d | 1.333 | .75 |
| Open: 208a-c<br>Closed: 208d | 1.143 | .875 |
| Open: 208d<br>Closed: 208a-c | 1 | 1 |
| Open: 208a, 208d<br>Closed: 208b, 208c | .889 | 1.125 |
| Open: 208b, 208d<br>Closed: 208a, 208c | .8 | 1.25 |
| Open: 208a, 208b, 208d<br>Closed: 208c | .727 | 1.375 |
| Open: 208c, 208d<br>Closed: 208a, 208b | .667 | 1.5 |
| Open: 208a, 208c, 208d<br>Closed: 208b | .615 | 1.625 |
| Open: 208b-d<br>Closed: 208a | .571 | 1.75 |
| Open: 208a-d<br>Closed: None | .533 | 1.875 |

As one skilled in the art will appreciate from the disclosure herein, the shunt 200 and other shunts described herein can have two, three, four, five, six, seven, eight, or more ports 208, each with a corresponding flow control element 211. Increasing the number of ports 208 generally increases the number of different drainage rates that can be implemented because as the number of ports 208 increases, the number of unique combinations of blocked and/unblocked ports increases as well. As described above, the ports 208 can also be selectively sized to provide the greatest number of potential therapy levels. For example, in embodiments with two ports, the ratio of the relative flow rates for the ports can be about 1:2 and/or the ratio of the relative resistances for the ports can be about 2:1 (e.g., producing a total of four discrete therapy levels). In other embodiments with two ports, the ratio of the relative flow rates is about 1:1 and/or the ratio of the relative resistances is about 1:1. In embodiments with three ports, the ratio of the relative flow rates for the ports can be about 1:2:4 and/or the ratio of the relative resistances for the ports can be about 4:2:1 (e.g., producing a total of eight discrete therapy levels). In other embodiments with three ports, the ratio of the relative flow rates is about 1:1:1 or about 1:2:3, and/or the ratio of the relative resistances is about 1:1:1 or about 3:2:1. In embodiments with four ports, the ratio of the relative flow rates for the ports can be about 1:2:4:8 and/or the ratio of the relative resistances for the ports can be about 8:4:2:1 (producing a total of sixteen discrete therapy levels). In other embodiments with four ports, the ratio of the relative flow rates is about 1:1:1:1 or about 1:2:3:4, and/or the ratio of the relative resistances is about 1:1:1:1 or about 4:3:2:1. In embodiments with five ports, the ratio of the relative flow rates for the ports can be about 1:2:4:8:16 and/or the ratio of the relative resistances for the ports can be about 16:8:4:2:1 (producing a total of thirty-two discrete therapy levels). In other embodiments with five ports, the ratio of the relative flow rates is about 1:1:1:1:1 or about 1:2:3:4:5, and/or the ratio of the relative resistances is about 1:1:1:1:1 or about 5:4:3:2:1.

Figure 3B:
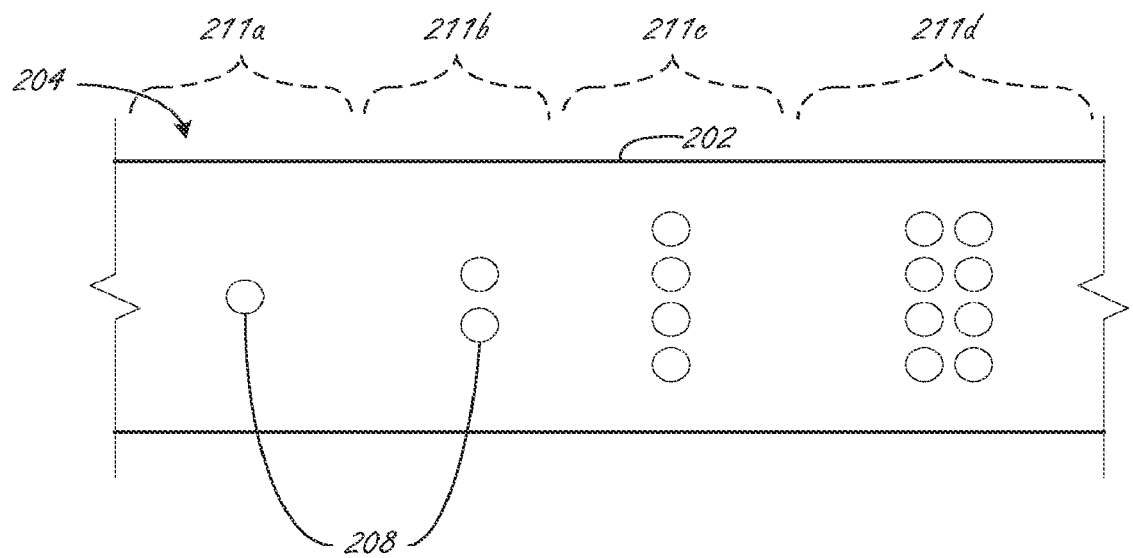
FIG. 3B illustrates select features of the shunt shown in FIGS. 2A-2C configured in accordance with embodiments of the present technology.

FIG. 3B illustrates another embodiment of the shunt 200 in which the number of ports 208 (e.g., apertures) corresponding to each flow control element 211a-d varies but a dimension of each port 208 is the same or at least generally the same. For example, the drainage element 202 can have one port 208 corresponding to the first flow control element 211a, two ports 208 corresponding to the second flow control element 211b, four ports 208 corresponding to the third flow control element 211c, and eight ports 208 corresponding to the fourth flow control element 211d. Because the dimensions of the ports 208 are the same or are at least generally the same, the ports 208 corresponding to the first flow control element 211a can provide a relative drainage rate of X, the ports 208 corresponding to the second flow control element 211b can provide a relative drainage rate of about 2X, the ports 208 corresponding to the third flow control element 211c can provide a relative drainage rate of about 4X, and the ports 208 corresponding to the flow control element 211d can provide a relative drainage rate of about 8X (e.g., the ratio of the relative flow rates between ports 208 remain 1:2:4:8). As described above, each of the flow control elements 211a-d can be individually actuated to block and/unblock the corresponding ports 208. As also described above, providing ports that facilitate the foregoing drainage rates increases the number of possible drainage rates while decreasing the number of flow control elements needed. In other embodiments, the number of ports 208 corresponding to each flow control elements 211a-d increases by one. In yet other embodiments, the ports 208 do not have the same dimensions.

In some embodiments, the shunt 200 may include a plurality of discrete and fluidly isolated lumens or channels associated with individual ports 208. In such embodiments, the therapy level (e.g., drainage rate, resistance, etc.) may be determined by the relative dimensions of the lumens, not the number or size of the ports 208. For example, each lumen may have a different dimension to impart a different flow resistance. In such embodiments, the shunt 200 can still include different size ports 208 (FIG. 3A) or different numbers of ports 208 (FIG. 3B) to provide a visual cue to a healthcare provide reflecting the relative fluid resistances of the corresponding channel (e.g., one aperture means the corresponding lumen has a first resistance, two apertures means the corresponding lumen has a second resistance less than the first resistance, etc.).

The above description primarily describes potential flow rates and resistances under a binary setting in which the ports 208a-d are either open or closed. However, in some embodiments, the gating elements 216 can be manipulated such that the ports 208a-d occupy one or more positions between fully open or fully closed. This can further increase the number of discrete therapy levels that the shunt 200 can provide. In yet other embodiments, the gating elements 216 may permit some fluid to leak through the ports 208a-d even in the closed positions (e.g., the gating elements 216 do not form a perfect fluid seal with the ports 208a-d when in the closed position).

Figure 4A:
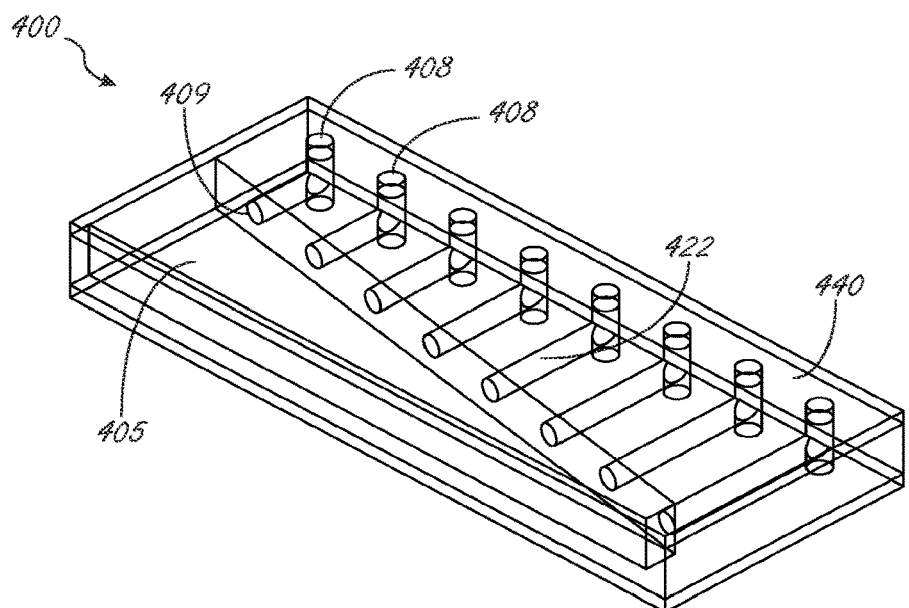
FIGS. 4A and 4B illustrate a drainage plate for use with an adjustable shunt configured in accordance with select embodiments of the present technology.
Figure 4B:
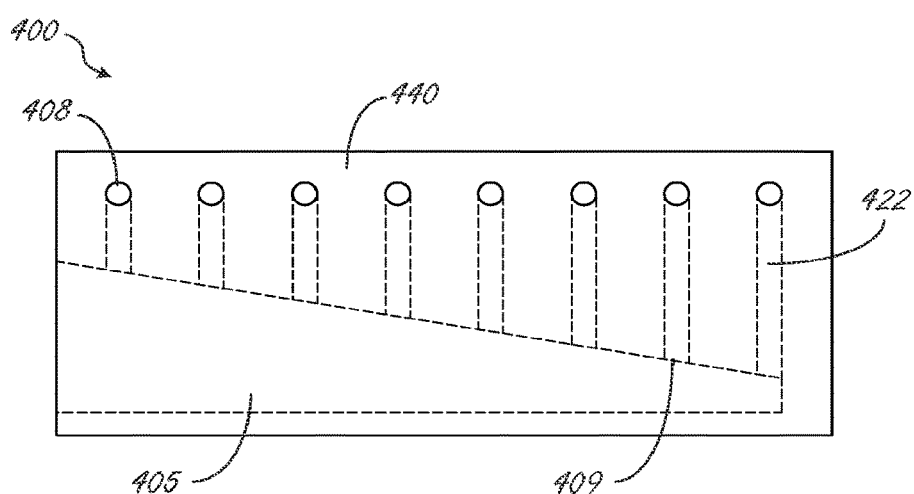

The techniques and actuation assemblies described above can also be used with other types of shunts and drainage elements. For example, FIGS. 4A and 4B illustrate select features of a shunt 400 having a drainage plate 440 configured in accordance with select embodiments of the present technology. More specifically, FIG. 4A is a partially isometric view of the plate 440 and FIG. 4B is a partially schematic top down view of the plate 440. The plate 440 includes a plurality of inflow ports 408 that permit fluid to flow into a plurality of corresponding channels 422. The channels 422 empty into a lumen 405 via a plurality of outflow ports 409. Accordingly, the plurality of inflow ports 408 and/or channels 422 are arranged as parallel fluid resistors, and can therefore exhibit similar flow characteristics as those described above with respect to the shunt 200 (FIGS. 2A-3B). The lumen 405 can direct fluid toward a desired outflow location (e.g., a bleb space) and/or an elongated drainage element (not shown).

The shunt 400 can include a flow control mechanism (not shown) operably coupled to the drainage plate 440 to control the flow of fluid through the channels 422. In some embodiments, the flow control mechanism includes a plurality of individually actuatable flow control elements associated with individual inflow ports 408 and channels 422. For example, in some embodiments, a flow control mechanism generally similar to the flow control mechanism 210 described with respect to FIGS. 2A-2C can be disposed over the plate 440 such that flow control elements 211a-d interface with the inflow ports 408. In some embodiments, aspects of the flow control mechanism 210 may be slightly modified to account for the different structure of the shunt 400. For example, the anchoring elements may not extend around the entirety of the shunt, but rather may be secured to an upper surface of the plate 440 (e.g., via welding, gluing or other suitable adhesives). Regardless of its configuration, the flow control mechanism can be positioned such that individual flow control elements (e.g., flow control elements 211a-d of FIGS. 2A-2C) are positioned to control the flow of fluid through individual ports 408. For example, the flow control elements 211a-d (FIGS. 2B and 2C) can be independently and selectively actuated to block and/or unblock flow through the corresponding channel 422. In other embodiments, other suitable flow control elements configured to at least partially block and/or unblock the flow of fluid through the channels 422 can be used.

In some embodiments, the channels 422 may each have the same or about the same flow resistance. In embodiments in which the channels 422 have the same or about the same flow resistance, opening additional channels 422 is expected to result in a stepwise increase in the drainage rate, and blocking additional channels 422 is expected to result in a stepwise decrease in the drainage rate. For example, moving from a single open channel 422 to two open channels 422 is expected to generally double the drainage rate, while moving from two open channels 422 to three open channels 422 is expected to generally increase the drainage rate by 50 percent. However, the total number of unique resistances and thus flow rates that can be achieved is not maximized, since the resistance and flow when only a first lumen is unblocked is the same as the resistance and flow when only a second lumen in unblocked.

In other embodiments, the channels 422 may have different resistances and thus different relative drainage rates. For example, in some embodiments, each individual channel 422 may be associated with a desired drainage rate and/or resistance relative to one another. For example, a first channel may be associated with a drainage rate of about X, a second channel may be associated with a drainage rate of about 2X, a third channel may be associated with a drainage rate of about 4X, and so on. As described above with reference to the ports 208, a greater number of drainage rates can be accomplished with fewer channels 422 when each channel 422 is associated with a different drainage rate. Flow resistance through the channels 422, and thus drainage rates through the channels 422, can be varied based on, for example, a length of the channel and/or a diameter of the channel. The length of the channel is generally proportional to the resistance of the channel, whereas the diameter of the channel is generally inversely proportional to the resistance of the channel. Accordingly, each individual channel 422 may have a unique length, diameter, or length and diameter combination that gives it a certain resistance. Individual channels 422 can then be selectively opened (or closed) to achieve a desired flow rate.

Figure 4C:
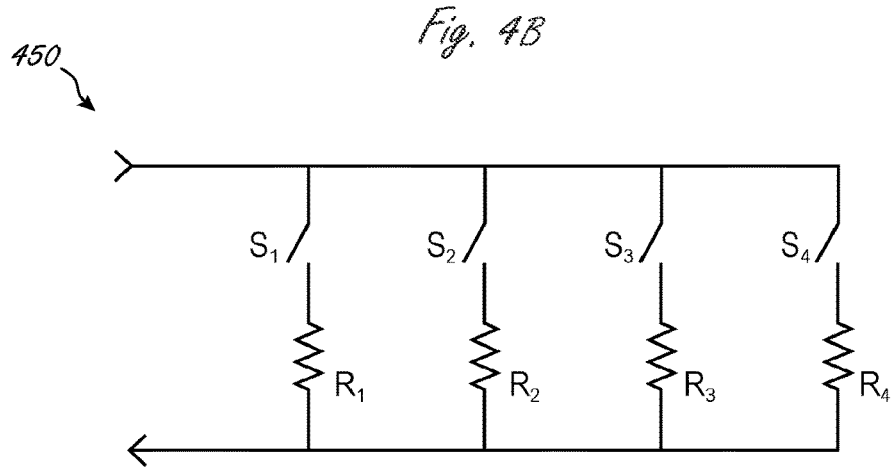
FIG. 4C is a schematic illustration of an electrical circuit having parallel resistors.

The flow characteristics through parallel fluid resistors such as the shunt 400 (and the shunt 200) can be similar to current flowing through an electrical circuit having a plurality of resistors arranged in parallel. FIG. 4C, for example, is a schematic illustration of an electrical circuit 650 having a plurality of resistors $R_{1-4}$ in parallel. Each resistor $R_{1-4}$ is analogous to an individual port or channel of a parallel resistor shunt (e.g., ports 208a-d of the shunt 200, ports 408 of the shunt 400, or channels 422 of the shunt 400). To control current flow through the circuit, a plurality of switches $S_{1-4}$ can complete or break the circuit through each individual resistor $R_{1-4}$. This is analogous to each individual port being transitionable between an open (e.g., blocked) and closed (e.g., unblocked) state. More than one switch $S_{1-4}$ being closed to complete the circuit 450 affects current flow through the circuit 450 in a similar manner as more than one port being open in a parallel resistor shunt. Although shown as having a current flowing through the circuit 450 in a first direction, the current could alternatively flow through the circuit 450 in a second direction opposite the first direction, similar to how the parallel resistor shunts described herein can operate with fluid flowing in either direction through the shunt.

Figure 5A:
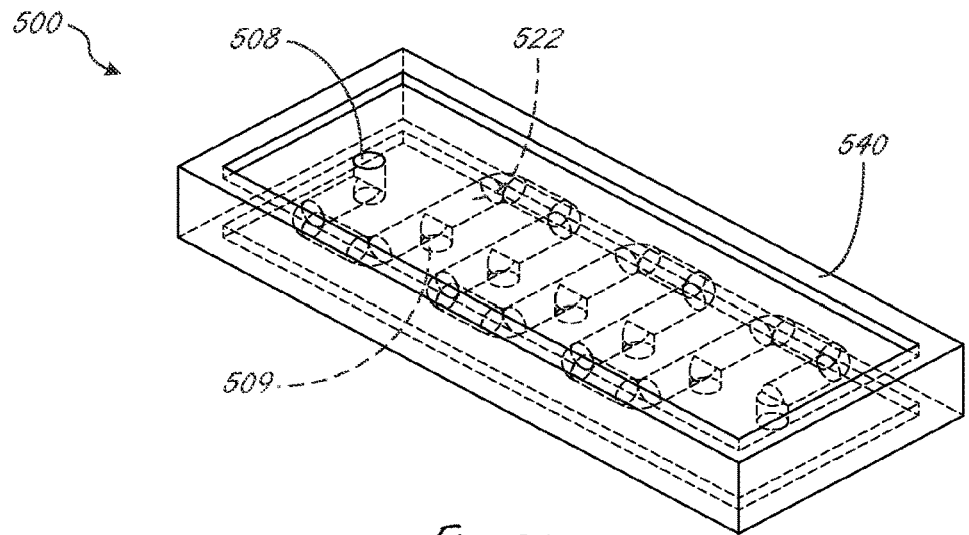
FIGS. 5A and 5B illustrate a drainage plate for use with an adjustable shunt configured in accordance with select embodiments of the present technology.
Figure 5B:
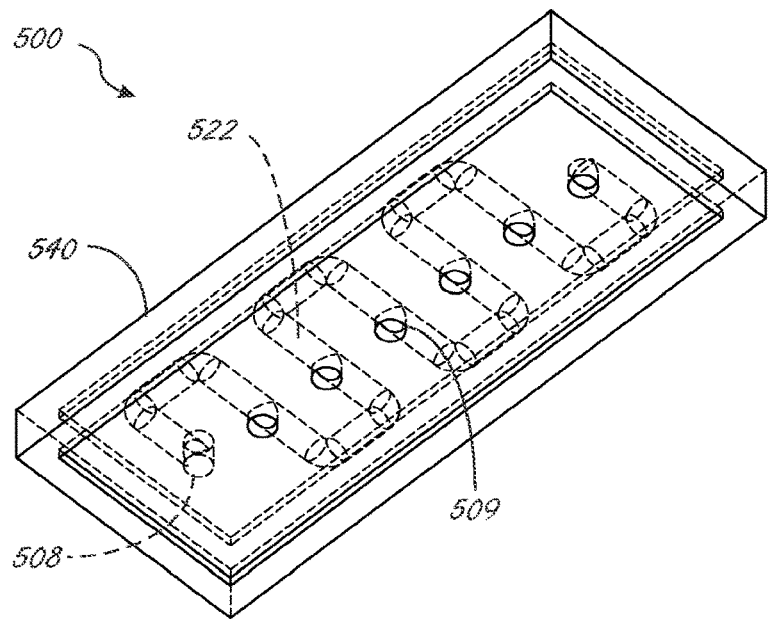

The present technology also provides shunting systems having a plurality of inflow ports operating as serial fluid resistors. For example, FIGS. 5A and 5B illustrate features of a shunt 500 having a drainage plate 540 and configured to act as a serial fluid resistor. More specifically, FIG. 5A is a top down partially isometric view of the drainage plate 540, and FIG. 5B is a bottom up partially isometric view of the drainage plate 540. Unlike the drainage plate 440 (FIG. 4A), the drainage plate 540 includes a single inflow port 508 allowing fluid to flow into a channel 522. The channel 522 includes a plurality of outflow ports 509 that allows fluid to flow out of the channel 522 and into a lumen (e.g., the lumen 405 described with respect to FIGS. 4A and 4B) that directs fluid toward a desired outflow location (e.g., a bleb space) and/or an elongated drainage element (not shown). The plurality of outflow ports 509 can be arranged in series along a length of the channel 522, and/or can be fluidly coupled to the channel 522 by a plurality of conduits extending from the channel 522. In other embodiments, the orientation of the drainage plate 540 can be reversed, such that fluid flows in the opposite direction (e.g., from the plurality of outflow ports 509 to the single inflow port 508).

The shunt 500 can include a flow control mechanism (not shown) operably coupled to the drainage plate 540 to control the flow of fluid out of the outflow ports 509 and into the lumen. The flow control mechanism can include a plurality of individually actuatable flow control elements associated with individual outflow ports 509. For example, in some embodiments, a flow control mechanism generally similar to the flow control mechanism 210 (FIGS. 2A-2C) described herein can be disposed on the plate 540 such that the flow control elements 211a-d interface with the outflow ports 509. In such embodiments, the plate 540 may be at least partially transmissive (e.g., transparent) to at least some forms of energy, such as laser energy having select wavelengths (e.g., between about 500 nm and about 600 nm, etc.). In other embodiments, other suitable flow control elements configured to at least partially block and/or unblock the flow of fluid through the outflow ports 509 can be used.

The plate 540 is configured to act as a serial resister. For example, the resistance is provided by the channel 522 (rather than the inflow port 508 and/or the outflow ports 509) and is based on the distance between the inflow port 508 and the closest open outflow port 509. For example, if the outflow port 509 spaced furthest apart from the inflow port 508 is the only outflow port 509 open, then the resistance to flow is the greatest (e.g., by virtue of the fluid having to travel the greatest distance through the channel 522). If the outflow port 509 closest to the inflow port 508 is open, then the resistance is the least (e.g., by virtue of the fluid having to travel the shortest distance through the channel 522). In such embodiments, the channels/apertures behave as if they are in series, and thus the number of discrete resistances and drainage rates is generally equal to the number of outflow apertures 509.

Figure 5C:
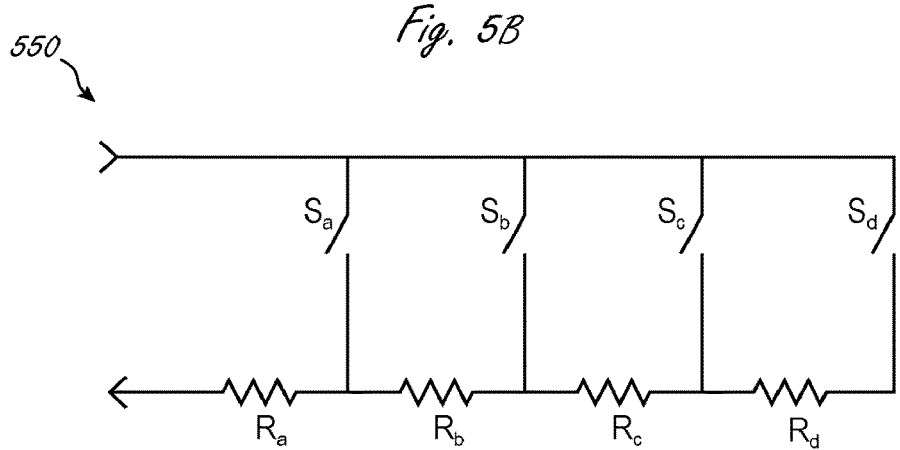
FIG. 5C is a schematic illustration of an electrical circuit having serial resistors.

The flow characteristics through serial fluid resistors such as the shunt 500 can be similar to current flowing through an electrical circuit having a plurality of resistors arranged in series. FIG. 5C, for example, is a schematic illustration of an electrical circuit 550 having a four resistors $R_{a-d}$ in series. Each resistor $R_{a-d}$ is analogous to an individual port of a serial resistor shunt (e.g., ports 509 of the shunt 500). To control current flow through the circuit, a plurality of switches Sa-d can complete or break the circuit. This is analogous to each individual port being transitionable between an open (e.g., blocked) and closed (e.g., unblocked) state. More than one switch Sa-d being closed to complete the circuit 550 affects current flow through the circuit 550 in a similar manner as more than one port being open in a serial resistor shunt. Although shown as having a current flowing through the circuit 650 in a first direction, the current could alternatively flow through the circuit 650 in a second direction opposite the first direction, similar to how the serial resistor shunts described herein can operate with fluid flowing in either direction through the shunt.

Figure 6:
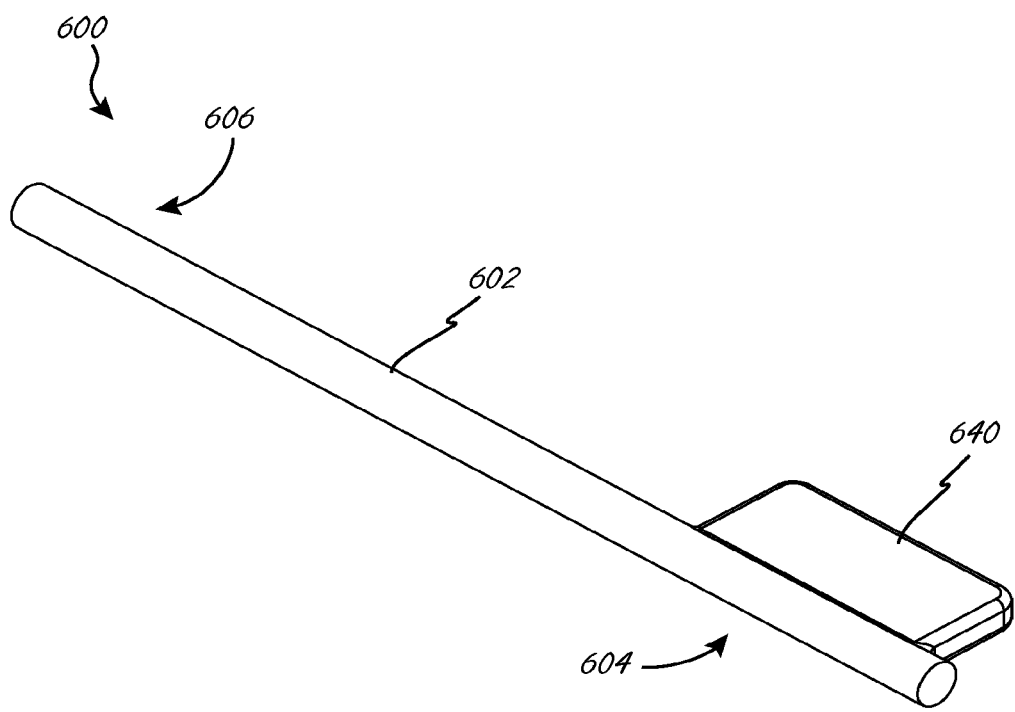
FIG. 6 illustrates a shunt configured in accordance with select embodiments of the present technology.

FIG. 6 is an isometric view of a shunt 600 configured in accordance with select embodiments of the present technology. The shunt 600 includes an elongated tube 602 having a first end portion 604 and a second end portion 606. The first end portion 604 is connected to a plate 640. The plate 640 can be generally similar to the plates 440 and/or 540 described above with respect to FIGS. 4A and 4B, and FIGS. 5A and 5B, respectively. The first end portion 604 can be fluidly coupled to an interior of the plate 640 (e.g., the lumen 405—FIG. 4A) and configured to receive fluid therefrom. The second end portion 606 can include one or more ports (not shown). When the shunt 600 is implanted in an eye, the first end portion 604 and the plate 640 can reside within an anterior chamber and the second end portion 606 can reside in a desired outflow location (e.g., a bleb space). In other embodiments, the first end portion 604 and the plate 640 can reside within the desired outflow location and the second end portion 606 can reside within the anterior chamber. Regardless of the orientation of the shunt 600, the shunt 600 is configured to drain aqueous from the anterior chamber when the shunt 600 is implanted in the eye. In some embodiments, the plate 640 may at least partially secure the shunt 600 in a desired position. The shunt 600 may optionally have additional features that help secure the shunt 600 in place when implanted in the eye. For example, the shunt 600 can include arms, anchors, plates, or other suitable features that secure the shunt 600 to native tissue.

The present technology further includes methods of shunting fluids through the shunting systems and shunts described herein (e.g., to drain aqueous from the anterior chamber for treating glaucoma). The methods can incorporate any of the techniques described above, including, for example, selectively actuating one or more flow control elements to open and/or close one or more ports (e.g. inflow ports) on a shunt to achieve a target resistance and/or flow. The methods may also include selectively actuating one or more flow control elements to open and/or close one or more ports until a target intraocular pressure is attained.

In some embodiments, the ports can all be simultaneously unblocked to provide the lowest resistance and highest flow for a given pressure. This may be done in a healthcare provider's office to quickly reduce intraocular pressure. Once a target intraocular pressure is achieved, some or all of the ports can be closed to provide a flow and resistance more suitable for chronic therapy. Without intending to be bound by theory, use of adjustable shunts such as those provided herein may be able to safely provide higher flow and lower resistance than conventional static (e.g., non-adjustable) shunts. For example, conventional static shunts generally do not provide high flow or low resistance in order to avoid inducing hypotony. In contrast, the shunts of the present technology can provide high flow and low resistance (e.g., by opening all the ports) that, if left unchanged for a prolonged period, could lead to hypotony. However, before hypotony occurs, a healthcare provider can adjust the shunt to lower flow and increase resistance. One expected advantage of this is that a healthcare provider can more quickly reduce intraocular pressure in the patient.

EXAMPLES

Several aspects of the present technology are set forth in the following examples:

1. A system for draining fluid, the system comprising:
a drainage element having a first end region positionable within a first body region and a second end region positionable within a second body region, wherein the first end region includes a first port, a second port, and a third port; and
a flow control mechanism for controlling the flow of fluid through the drainage element, the flow control mechanism including—
a first flow control element moveable between a first open position permitting fluid to flow into the drainage element via the first port and a first closed position substantially preventing fluid from flowing into the drainage element via the first port,
a second flow control element moveable between a second open position permitting fluid to flow into the drainage element via the second port and a second closed position substantially preventing fluid from flowing into the drainage element via the second port, and
a third flow control element moveable between a third open position permitting fluid to flow into the drainage element via the third port and a third closed position substantially preventing fluid from flowing into the drainage element via the third port,
wherein the first flow control element, the second flow control element, and the third flow control element are independently moveable between their respective open and closed positions.

2. The system of example 1 wherein:
when the first flow control element is in the first open position, the second flow control element is in the second closed position, and the third flow control element is in the third closed position, the system is configured to provide a first relative resistance to fluid flow;
when the second flow control element is in the second open position, the first flow control element is in the first closed position, and the third flow control element is in the third closed position, the system is configured to provide a second relative resistance; and
when the third flow control element is in the third open position, the first flow control element is in the first closed position, and the second flow control element is in the second closed position, the system is configured to provide a third relative resistance.

3. The system of example 2 wherein the second relative resistance is less than the first relative resistance, and wherein the third relative resistance is less than the first relative resistance 4. The system of example 3 wherein a ratio between the first relative resistance, the second relative resistance, and the third relative resistance is about 4:2:1.

5. The system of example 3 wherein a ratio between the first relative resistance, the second relative resistance, and the third relative resistance is about 3:2:1.

6. The system of example 2 wherein a ratio between the first relative resistance, the second relative resistance, and the third relative resistance is about 1:1:1.

7. The system of example 1 wherein:
when the first flow control element is in the first open position, the second flow control element is in the second closed position, and the third flow control element is in the third closed position, the system is configured to provide a first relative drainage rate;
when the second flow control element is in the second open position, the first flow control element is in the first closed position, and the third flow control element is in the third closed position, the system is configured to provide a second relative drainage rate; and
when the third flow control element is in the third open position, the first flow control element is in the first closed position, and the second flow control element is in the second closed position, the system is configured to provide a third relative drainage rate.

8. The system of example 7 wherein the second relative drainage rate is greater than the first relative drainage rate, and wherein the third relative drainage rate is greater than the second relative drainage rate.

9. The system of example 8 wherein a ratio between the first relative drainage rate, the second relative drainage rate, and the third relative drainage rate is about 1:2:4.

10. The system of example 8 wherein a ratio between the first relative drainage rate, the second relative drainage rate, and the third relative drainage rate is about 1:2:3.

11. The system of example 7 wherein a ratio between the first relative drainage rate, the second relative drainage rate, and the third relative drainage rate is about 1:1:1.

12. The system of any of examples 1-11 wherein the drainage element has a first channel fluidly coupled to the first port, a second channel fluidly coupled to the second port, and a third channel fluidly coupled to the third port.

13. The system of example 12 wherein the first channel is configured to provide a greater relative resistance than the second channel, and wherein the second channel is configured to provide a greater relative resistance than the third channel.

14. The system of example 13 wherein the first channel has a first cross sectional area, the second channel has a second cross sectional area greater than the first cross sectional area, and the third channel has a third cross sectional area greater than the second cross sectional area.

15. The system of any of examples 1-14 wherein the first port has a first area, the second port has a second area greater than the first area, and the third port has a third area greater than the second area.

16. The system of any of examples 1-15 wherein the first port includes a single aperture, the second port includes two apertures, and the third port includes three or more apertures.

17. The system of any of examples 1-16 wherein the first port is a first inflow port, the second port is a second inflow port, and the third port is a third inflow port.

18. The system of any of examples 1-17 wherein the first body region is an anterior chamber, and wherein the fluid is aqueous.

19. A system for draining fluid, the system comprising:
a drainage element having a first end region positionable within a first body region and a second end region positionable within a second body region, wherein the first end region includes a first inflow port and a second inflow port, and wherein—
when the first inflow port is unblocked and the second inflow port is blocked, the system is configured to provide a first relative drainage rate through the drainage element, and when the second inflow port is unblocked and the first inflow port is blocked, the system is configured to provide a second relative drainage rate through the drainage element greater than the first relative drainage rate;

a flow control mechanism, including—
 a first flow control element configured to selectively control the flow of fluid through the first inflow port, and
 a second flow control element configured to selectively control the flow of fluid through the second inflow port,
 wherein the first flow control element and the second flow control element are independently actuatable.

20. The system of example 19 wherein the ratio between the first relative drainage rate and the second relative drainage rate is 1:2.

21. The system of example 20 wherein when both the first inflow port and the second inflow port are unblocked, the system is configured to provide a third relative drainage rate through the drainage element that is greater than the first relative drainage rate and the second relative drainage rate.

22. The system of example 21 wherein a ratio between the first, second, and third relative drainage rates is 1:2:3.

23. The system of any of examples 19-22 wherein the first inflow port includes a single aperture and the second inflow port includes a plurality of apertures.

24. The system of any of examples 19-23 wherein the first inflow port has a first area and the second inflow port has a second area greater than the first area.

25. The system of any of examples 19-24 wherein the drainage element includes (i) a first lumen extending between the first inflow port and the second end region, and (ii) a second lumen extending between the second inflow port and the second end region, and wherein the first lumen is configured to provide a different resistance to fluid flow than the second lumen.

26. The system of any of examples 19-25 wherein the drainage element further comprises a third inflow port, and wherein when the third inflow port is unblocked and the first and second inflow ports are blocked, the system is configured to provide a third relative drainage rate through the drainage element.

27. The system of example 26 wherein a ratio between the first relative drainage rate, the second relative drainage rate, and the third relative drainage rate is about 1:2:3.

28. The system of example 26 wherein a ratio between the first relative drainage rate, the second relative drainage rate, and the third relative drainage rate is about 1:2:4.

29. The system of example 25 wherein the drainage element further comprises a fourth inflow port, and wherein when the fourth inflow port is unblocked and the first, second, and third inflow ports are blocked, the system is configured to provide a fourth relative drainage rate through the drainage rate, and wherein a ratio between the first, second, third, and fourth relative drainage rates is about 1:2:4:8.

30. The system of any of examples 19-29 wherein the first body region is an anterior chamber of an eye, and wherein the fluid is aqueous.

31. The system of any of examples 19-30 wherein the drainage element includes a plate extending from the first end portion, and wherein the plate includes the first and second inflow ports.

32. An adjustable shunt, comprising:
 a drainage element having a first end portion positionable within an anterior chamber of an eye of a patient and a second end portion positionable within a target outflow location of the patient, wherein—
  the first end portion includes at least three inflow ports, wherein the first inflow port is configured to provide a first drainage rate when only the first inflow port is open, the second inflow port is configured to provide a second drainage rate greater than the first drainage rate when only the second inflow port is open, and the third inflow port is configured to provide a third drainage rate greater than the second drainage rate when only the third inflow port is open,
  the second end portion includes at least one outflow port, and
  a lumen extends through the drainage element from the first end portion to the second end portion to fluidly connect the at least three inflow ports and the at least one outflow port; and
 a flow control mechanism having at least three individually actuatable flow control elements, wherein the first flow control element is selectively operable to block and unblock the first inflow port, the second flow control element is selectively operable to block and unblock the second inflow port, and the third flow control element is selectively operable to block and unblock the third inflow port.

33. The adjustable shunt of example 32 wherein the first drainage rate, the second drainage rate, and the third drainage rate are predetermined relative drainage rates, and wherein the first drainage rate is about X, the second drainage rate is about 2X, and the third drainage rate is about 3X.

34. The adjustable shunt of example 32 wherein the first drainage rate, the second drainage rate, and the third drainage rate are predetermined relative drainage rates, and wherein the first drainage rate is about X, the second drainage rate is about 2X, and the third drainage rate is about 4X.

35. The adjustable shunt of example 34 wherein, when more than one inflow port is open, the shunt is configured to provide a fourth relative drainage rate that is different than the first drainage rate, the second drainage rate, and the third drainage rate.

36. The adjustable shunt of example 34 wherein the shunt is configured to provide additional predetermined relative drainage rates including—
 a fourth drainage rate of about 3X when only the first inflow port and the second inflow port are open;
 a fifth drainage rate of about 5X when only the first inflow port and the third inflow port are open;
 a sixth drainage rate of about 6X when only the second inflow port and the third inflow port are open; and
 a seventh drainage rate of about 7X when the first inflow port, the second inflow port, and the third inflow port are open.

37. The adjustable shunt of example 36 wherein the flow control elements are selectively actuatable to achieve any of the predetermined relative drainage rates.

38. A method of treating glaucoma, the method comprising:
 draining aqueous from an anterior chamber of an eye to a target outflow location using an adjustable shunt, wherein the adjustable shunt includes—
  a first inflow port fluidly coupled to an interior of the shunt,
  a second inflow port fluidly coupled to the interior of the shunt;

a first flow control element moveable between a first open position permitting fluid to flow into the shunt via the first inflow port and a first closed position substantially preventing fluid from flowing into the shunt via the first inflow port, and a second flow control element moveable between a second open position permitting fluid to flow into the shunt via the first inflow port and a second closed position substantially preventing fluid from flowing into the shunt via the first inflow port;

selectively adjusting the drainage rate of the aqueous by actuating the first flow control element and/or the second flow control element between their respective open and closed positions.

39. The method of example 38 wherein the first inflow port provides a first drainage rate when only the first inflow port is unblocked, and wherein the second inflow port provides a second drainage rate greater than the first drainage rate when only the second inflow port is unblocked.

40. The method of example 38 or 39 wherein actuating at least one of the individually actuatable flow control elements comprises applying energy to at least one of the individually actuatable flow control elements.

41. The method of example 40 wherein the energy is non-invasive energy.

42. An adjustable shunt, comprising:

a drainage element having a first end portion positionable within an anterior chamber of an eye of a patient and a second end portion positionable within a target outflow location of the patient, wherein— the first end portion includes a plurality of inflow ports, the plurality of inflow ports including at least a first inflow port and a second inflow port, the second end portion includes at least one outflow port, and a lumen extends through the drainage element from the first end portion to the second end portion to fluidly connect the plurality of inflow ports and the at least one outflow port; and a flow control mechanism configured to control the flow of fluid through the plurality of inflow ports, wherein the flow control mechanism includes— a first flow control element configured to control the flow of fluid through the first inflow port, and a second flow control element configured to control the flow of fluid through the second inflow port, wherein the first flow control element and the second flow control element are individually actuatable such that the first flow control element is configured to move independent of the second flow control element to selectively block and/or unblock the first inflow port and the second flow control element is configured to move independent of the first flow control element to selectively block and/or unblock the second inflow port.

43. The adjustable shunt of example 42 wherein the first inflow port and the second inflow port have different diameters.

44. The adjustable shunt of example 42 wherein the first inflow port comprises a single inflow aperture and the second inflow port comprises at least two inflow apertures.

45. The adjustable shunt of any of examples 42-44 wherein the first inflow port is configured to provide a first drainage rate through the shunt when only the first inflow port is unblocked, and wherein the second inflow port is configured to provide a second drainage rate through the shunt that is greater than the first drainage rate when only the second inflow port is unblocked.

46. The adjustable shunt of any of examples 42-45 wherein the drainage element includes a plate extending from the first end portion, and wherein the plate includes the plurality of inflow ports.

47. The adjustable shunt of example 46 wherein the plate includes— a first channel fluidly connecting the first inflow port and the lumen; and a second channel fluidly connecting the second inflow port and the lumen, wherein the first channel is separate from the second channel.

48. The adjustable shunt of example 47 wherein the first flow control element is positioned between the first channel and the lumen, and wherein the second flow control element is positioned between the second channel and the lumen.

49. The adjustable shunt of example 47 wherein the first channel extends between the first flow control element and the lumen, and wherein the second channel extends between the second flow control element and the lumen.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for draining fluid, the system comprising:
a drainage element having a first end region positionable within a first body region and a second end region positionable within a second body region, wherein the first end region includes a first port, a second port, and a third port; and
a flow control mechanism for controlling the flow of fluid through the drainage element, the flow control mechanism including—
a first flow control element moveable between a first open position permitting fluid to flow into the drainage element via the first port and a first closed position substantially preventing fluid from flowing into the drainage element via the first port,
a second flow control element moveable between a second open position permitting fluid to flow into the drainage element via the second port and a second closed position substantially preventing fluid from flowing into the drainage element via the second port, and
a third flow control element moveable between a third open position permitting fluid to flow into the drainage element via the third port and a third closed position substantially preventing fluid from flowing into the drainage element via the third port,
wherein the first flow control element, the second flow control element, and the third flow control element are each independently and repeatably moveable between their respective open and closed positions.

2. The system of claim 1 wherein:
when the first flow control element is in the first open position, the second flow control element is in the second closed position, and the third flow control element is in the third closed position, the system is configured to provide a first relative resistance to fluid flow;
when the second flow control element is in the second open position, the first flow control element is in the first closed position, and the third flow control element is in the third closed position, the system is configured to provide a second relative resistance; and
when the third flow control element is in the third open position, the first flow control element is in the first closed position, and the second flow control element is in the second closed position, the system is configured to provide a third relative resistance.

3. The system of claim 2 wherein the second relative resistance is less than the first relative resistance, and wherein the third relative resistance is less than the first relative resistance.

4. The system of claim 3 wherein a ratio between the first relative resistance, the second relative resistance, and the third relative resistance is about 4:2:1.

5. The system of claim 3 wherein a ratio between the first relative resistance, the second relative resistance, and the third relative resistance is about 3:2:1.

6. The system of claim 2 wherein a ratio between the first relative resistance, the second relative resistance, and the third relative resistance is about 1:1:1.

7. The system of claim 1 wherein:
when the first flow control element is in the first open position, the second flow control element is in the second closed position, and the third flow control element is in the third closed position, the system is configured to provide a first relative drainage rate;
when the second flow control element is in the second open position, the first flow control element is in the first closed position, and the third flow control element is in the third closed position, the system is configured to provide a second relative drainage rate; and
when the third flow control element is in the third open position, the first flow control element is in the first closed position, and the second flow control element is in the second closed position, the system is configured to provide a third relative drainage rate.

8. The system of claim 7 wherein the second relative drainage rate is greater than the first relative drainage rate, and wherein the third relative drainage rate is greater than the second relative drainage rate.

9. The system of claim 8 wherein a ratio between the first relative drainage rate, the second relative drainage rate, and the third relative drainage rate is about 1:2:4.

10. The system of claim 8 wherein a ratio between the first relative drainage rate, the second relative drainage rate, and the third relative drainage rate is about 1:2:3.

11. The system of claim 7 wherein a ratio between the first relative drainage rate, the second relative drainage rate, and the third relative drainage rate is about 1:1:1.

12. The system of claim 1 wherein the drainage element has a first channel fluidly coupled to the first port, a second channel fluidly coupled to the second port, and a third channel fluidly coupled to the third port.

13. The system of claim 12 wherein the first channel is configured to provide a greater relative resistance than the second channel, and wherein the second channel is configured to provide a greater relative resistance than the third channel.

14. The system of claim 13 wherein the first channel has a first cross sectional area, the second channel has a second cross sectional area greater than the first cross sectional area, and the third channel has a third cross sectional area greater than the second cross sectional area.

15. The system of claim 1 wherein the first port has a first area, the second port has a second area greater than the first area, and the third port has a third area greater than the second area.

16. The system of claim 1 wherein the first port includes a single aperture, the second port includes two apertures, and the third port includes three or more apertures.

17. The system of claim 1 wherein the first port is a first inflow port, the second port is a second inflow port, and the third port is a third inflow port.

18. The system of claim 1 wherein the first body region is an anterior chamber, and wherein the fluid is aqueous.

19. The system of claim 1 wherein
the first flow control element is selectively moveable between the first closed position and the first open position regardless of a position of the second flow control element and the third flow control element;

the second flow control element is selectively moveable between the second closed position and the second open position regardless of a position of the first flow control element and the third flow control element; and the third flow control element is selectively moveable between the third closed position and the third open position regardless of a position of the first flow control element and the second flow control element.

20. The system of claim 1 wherein:
a position of the first flow control element is independent of a position of the second flow control element and the third flow control element;
a position of the second flow control element is independent of a position of the first flow control element and the third flow control element, and
a position of the third flow control element is independent of a position of the first flow control element and the second flow control element.

21. The system of claim 1 wherein:
when in the first closed position, the first flow control element seals the first port to prevent fluid from flowing therethrough,
when in the second closed position, the second flow control element seals the second port to prevent fluid from flowing therethrough, and
when in the third closed position, the third flow control element seals the third port to prevent fluid from flowing therethrough.

22. A system for draining fluid, the system comprising:
a drainage element having a first end region positionable within a first body region and a second end region positionable within a second body region, wherein the first end region includes a first inflow port and a second inflow port, and wherein—
when the first inflow port is unblocked and the second inflow port is blocked, the system is configured to provide a first relative drainage rate through the drainage element, and
when the second inflow port is unblocked and the first inflow port is blocked, the system is configured to provide a second relative drainage rate through the drainage element greater than the first relative drainage rate;
a flow control mechanism, including—
a first flow control element configured to selectively control the flow of fluid through the first inflow port, and
a second flow control element configured to selectively control the flow of fluid through the second inflow port,
wherein the first flow control element and the second flow control element are independently and repeatably actuatable.

23. The system of claim 22 wherein the ratio between the first relative drainage rate and the second relative drainage rate is 1:2.

24. The system of claim 23 wherein when both the first inflow port and the second inflow port are unblocked, the system is configured to provide a third relative drainage rate through the drainage element that is greater than the first relative drainage rate and the second relative drainage rate.

25. The system of claim 24 wherein a ratio between the first, second, and third relative drainage rates is 1:2:3.

26. The system of claim 22 wherein the first inflow port includes a single aperture and the second inflow port includes a plurality of apertures.

27. The system of claim 22 wherein the first inflow port has a first area and the second inflow port has a second area greater than the first area.

28. The system of claim 22 wherein the drainage element includes (i) a first lumen extending between the first inflow port and the second end region, and (ii) a second lumen extending between the second inflow port and the second end region, and wherein the first lumen is configured to provide a different resistance to fluid flow than the second lumen.

29. The system of claim 28 wherein the drainage element further comprises a fourth inflow port, and wherein when the fourth inflow port is unblocked and the first, second, and third inflow ports are blocked, the system is configured to provide a fourth relative drainage rate through the drainage rate, and wherein a ratio between the first, second, third, and fourth relative drainage rates is about 1:2:4:8.

30. The system of claim 22 wherein the drainage element further comprises a third inflow port, and wherein when the third inflow port is unblocked and the first and second inflow ports are blocked, the system is configured to provide a third relative drainage rate through the drainage element.

31. The system of claim 30 wherein a ratio between the first relative drainage rate, the second relative drainage rate, and the third relative drainage rate is about 1:2:3.

32. The system of claim 30 wherein a ratio between the first relative drainage rate, the second relative drainage rate, and the third relative drainage rate is about 1:2:4.

33. The system of claim 22 wherein the first body region is an anterior chamber of an eye, and wherein the fluid is aqueous.

34. The system of claim 22 wherein the drainage element includes a plate extending from the first end portion, and wherein the plate includes the first and second inflow ports.

35. An adjustable shunt, comprising:
a drainage element having a first end portion positionable within an anterior chamber of an eye of a patient and a second end portion positionable within a target outflow location of the patient, wherein—
the first end portion includes at least three inflow ports, wherein the first inflow port is configured to provide a first drainage rate when only the first inflow port is open, the second inflow port is configured to provide a second drainage rate greater than the first drainage rate when only the second inflow port is open, and the third inflow port is configured to provide a third drainage rate greater than the second drainage rate when only the third inflow port is open,
the second end portion includes at least one outflow port, and
a lumen extends through the drainage element from the first end portion to the second end portion to fluidly connect the at least three inflow ports and the at least one outflow port; and
a flow control mechanism having at least three individually actuatable flow control elements, wherein the first flow control element is selectively operable to repeatably block and unblock the first inflow port, the second flow control element is selectively operable to repeatably block and unblock the second inflow port, and the third flow control element is selectively operable to repeatably block and unblock the third inflow port.

36. The adjustable shunt of claim 35 wherein the first drainage rate, the second drainage rate, and the third drainage rate are predetermined relative drainage rates, and wherein the first drainage rate is about X, the second drainage rate is about 2X, and the third drainage rate is about 3X.

37. The adjustable shunt of claim 35 wherein the first drainage rate, the second drainage rate, and the third drainage rate are predetermined relative drainage rates, and wherein the first drainage rate is about X, the second drainage rate is about 2X, and the third drainage rate is about 4X.

38. The adjustable shunt of claim 37 wherein, when more than one inflow port is open, the shunt is configured to provide a fourth relative drainage rate that is different than the first drainage rate, the second drainage rate, and the third drainage rate.

39. The adjustable shunt of claim 37 wherein the shunt is configured to provide additional predetermined relative drainage rates including—
a fourth drainage rate of about 3X when only the first inflow port and the second inflow port are open;
a fifth drainage rate of about 5X when only the first inflow port and the third inflow port are open;
a sixth drainage rate of about 6X when only the second inflow port and the third inflow port are open; and
a seventh drainage rate of about 7X when the first inflow port, the second inflow port, and the third inflow port are open.

40. The adjustable shunt of claim 39 wherein the flow control elements are selectively actuatable to achieve any of the predetermined relative drainage rates.

41. A method of treating glaucoma, the method comprising:
draining aqueous from an anterior chamber of an eye to a target outflow location using an adjustable shunt, wherein the adjustable shunt includes—
a first inflow port fluidly coupled to an interior of the shunt,
a second inflow port fluidly coupled to the interior of the shunt;
a first flow control element repeatably moveable between a first open position permitting fluid to flow into the shunt via the first inflow port and a first closed position substantially preventing fluid from flowing into the shunt via the first inflow port, and
a second flow control element repeatably moveable between a second open position permitting fluid to flow into the shunt via the first inflow port and a second closed position substantially preventing fluid from flowing into the shunt via the first inflow port,
wherein the first flow control element and the second flow control element are independently moveable with respect to each other; and
selectively adjusting the drainage rate of the aqueous by actuating the first flow control element and/or the second flow control element between their respective open and closed positions.

42. The method of claim 41 wherein the first inflow port provides a first drainage rate when only the first inflow port is unblocked, and wherein the second inflow port provides a second drainage rate greater than the first drainage rate when only the second inflow port is unblocked.

43. The method of claim 41 wherein actuating at least one of the individually actuatable flow control elements comprises applying energy to at least one of the individually actuatable flow control elements.

44. The method of claim 43 wherein the energy is non-invasive energy.

\* \* \* \* \*